United States Patent [19]

Kawashima

[11] Patent Number: 5,078,681
[45] Date of Patent: Jan. 7, 1992

[54] BALLOON CATHETER APPARATUS WITH RELEASABLE DISTAL SEAL AND METHOD OF OPERATION

[75] Inventor: Masahiro Kawashima, Hino, Japan

[73] Assignee: Olympus Optical Co., Ltd., Tokyo, Japan

[21] Appl. No.: 426,892

[22] Filed: Oct. 23, 1989

[51] Int. Cl.⁵ .................................. A61M 25/02
[52] U.S. Cl. ............................ 604/53; 604/99; 604/96
[58] Field of Search ............... 604/52, 53, 96-98, 604/158, 164, 171, 264, 99; 128/772, 656-658

[56] References Cited

U.S. PATENT DOCUMENTS

| | | | |
|---|---|---|---|
| 3,640,282 | 2/1972 | Kamen et al. | 604/96 X |
| 3,905,361 | 9/1975 | Hewson et al. | 604/96 X |
| 3,913,565 | 10/1975 | Kawanara | 128/772 |
| 4,029,104 | 6/1977 | Kerber | 128/348 |
| 4,798,586 | 1/1989 | Stevens | 604/96 |
| 4,813,934 | 3/1989 | Engelson et al. | 604/99 |
| 4,875,897 | 10/1989 | Lee | 606/15 X |
| 4,921,478 | 5/1990 | Solano et al. | 604/53 |
| 4,932,959 | 6/1990 | Horzewski et al. | 606/194 |

FOREIGN PATENT DOCUMENTS

| | | |
|---|---|---|
| 2817972A1 | 4/1978 | Fed. Rep. of Germany. |
| 2934841A1 | 8/1979 | Fed. Rep. of Germany. |
| 3326648C2 | 2/1985 | Fed. Rep. of Germany. |
| 8511340 | 7/1985 | Fed. Rep. of Germany. |
| 3538739A1 | 10/1985 | Fed. Rep. of Germany. |
| 221354A1 | 4/1985 | German Democratic Rep.. |
| 59-161119 | 10/1984 | Japan. |
| 61-293416 | 12/1986 | Japan. |
| WO89/00829 | 2/1989 | Japan. |

*Primary Examiner*—C. Fred Rosenbaum
*Assistant Examiner*—Corrine Maglione
*Attorney, Agent, or Firm*—Frishauf, Holtz, Goodman & Woodward

[57] ABSTRACT

A balloon catheter apparatus is used in combination with an endoscope having an insertion portion to be inserted in a body cavity. The apparatus comprises a catheter to be connected to a manipulating section, the catheter including an elongated tube through which the insertion portion is inserted, and in which a liquid is fed. The tube includes a balloon capable of being inflated outward in accordance with a liquid pressure in the tube, a first cylindrical portion for connecting the balloon to the manipulating section and defining a liquid path together with the inserted insertion portion, and a second cylindrical portion, which is connected to the balloon, and through which a distal end portion of the insertion portion is caused to protrude outward. The second cylindrical portion is brought into contact with the insertion portion to provide an elastic liquid-tight seal between the second cylindrical portion and the insertion portion. The seal is released by a liquid pressure in the liquid path which exceeds a predetermined liquid pressure, thereby feeding the liquid in the liquid path outward through the second cylindrical portion.

12 Claims, 5 Drawing Sheets

BALLOON CATHETER APPARATUS WITH RELEASABLE DISTAL SEAL AND METHOD OF OPERATION

BACKGROUND OF THE INVENTION

1. Field of the Invention

The present invention relates to a balloon catheter apparatus to be used in combination with a body cavity insertion device such as an endoscope or a laser probe.

2. Description of the Related Art

In a conventional technique, when, for example, the inside of the cavity of a vessel, such as a blood vessel, in which an opaque liquid flows is to be observed, the opaque liquid in the vessel cavity is replaced with a transparent liquid such as a physiological saline solution so as to ensure an observation field. Published Unexamined Japanese Utility Model Application No. 59-161119 discloses such a conventional technique.

In the above-described conventional technique, a liquid path is formed in the insertion portion of the endoscope, and a transparent liquid is flushed through the path to ensure a field of view. However, a blood flow cannot be blocked by simply flushing the transparent liquid from the distal end of the insertion portion. Hence, it is very difficult to keep a good field of view.

Published Unexamined Japanese Patent Application No. 61-293416, therefore, discloses a technique for blocking a blood flow from the upstream side in a blood vessel. In this conventional technique, a blood flow blocking balloon is arranged at the distal end of the insertion portion of an endoscope, and an inflation fluid source is connected to one end of a first tube which is inserted in the insertion portion. The other end of the first tube communicates with the inside of the balloon. A second tube is inserted in the insertion portion while one end of the tube is open to the distal end of the insertion portion and the other is connected to a transparent fluid source. A liquid is supplied from the inflation fluid source to the balloon to inflate it so as to block the blood flow from the upstream side. In this state, a transparent liquid is caused to flow from the transparent fluid source in order to ensure a field of view.

By blocking a blood flow with a balloon and replacing an opaque liquid with a transparent liquid in this manner, a good field of view can be ensured. In the above described conventional technique, however, the two tubes respectively used for supplying liquids from the inflation and transparent fluid sources must be inserted in the insertion portion. Therefore, the insertion portion is inevitably increased in size and cannot be suitably used especially for a narrow vessel such as a blood vessel. In addition, in order to ensure a good field of view, the inflation fluid source for inflating the balloon and the transparent fluid source for supplying a transparent liquid which are arranged at the proximal end of the insertion portion must be operated in a predetermined order. This complicates the operation. Moreover, an operation error tends to occur.

SUMMARY OF THE INVENTION

It is an object of the present invention to provide a balloon catheter apparatus which is free from an increase in size and can ensure a good field of view with a simple operation.

According to the present invention, there is provided a balloon catheter apparatus to be used in combination with a body cavity insertion device having an insertion portion to be inserted in a body cavity, comprising, a manipulating section having a first reception portion for receiving the insertion portion therein and a liquid port capable of feeding a liquid to the reception portion, and a catheter to be connected to the manipulating section, the catheter including an elongated tube defining a second reception portion, which communicates with the first reception portion, through which the insertion portion is inserted, and in which a liquid is fed through the liquid port, the tube including a balloon having distal and proximal ends and capable of being inflated outward in accordance with a liquid pressure in the second reception portion, a first cylindrical portion for connecting the proximal end of the balloon to the first reception portion and defining a liquid path together with the inserted insertion portion, and a second cylindrical portion, which is connected to the distal end of the balloon, and through which a distal end portion of the insertion portion is caused to protrude outward, the second cylindrical portion being brought into contact with the insertion portion to provide a liquid-tight seal between itself and the insertion portion, and the seal being released by a liquid pressure in the second reception portion which exceeds a predetermined liquid pressure, thereby feeding the liquid in the second reception portion outward through the second cylindrical portion.

According to the above-described arrangement, by simply feeding a liquid from the feed port, the balloon can be inflated, and a liquid in a body cavity can be replaced with another liquid.

BRIEF DESCRIPTION OF THE DRAWINGS

FIGS. 1 to 6 show the first embodiment of the present invention, in which

DETAILED DESCRIPTION OF THE PREFERRED EMBODIMENTS

The first embodiment of the present invention will be described below with reference to FIGS. 1 to 6. A balloon catheter apparatus 1 shown in FIG. 1 comprises a manipulating section 2. A first path 4 constituting a first insertion portion and a second path 5 as a feed port are formed in a cylindrical body 3 of the manipulating section 2. The first path 4 extends in the axial direction of the body 3, and its both ends are open. The second path 5 extends perpendicular to and communicates with the first path 4. A step is formed in the inner surface of the proximal end portion of the first path 4 so as to form a large-diameter portion 6. An O-ring 7 is fitted in the large-diameter portion 6 so as to protrude inward from the inner surface of the path 4. The O-ring 7 extends coaxially with the first path 4 and is clamped and held between a projection of a first cap 8, in which a through hole 8a communicating with the O-ring 7 is formed, and the step. The first cap 8 is threadably engaged with a first threaded portion 3a formed on the outer surface at one end portion of the body 3. The O-ring 7 and the through hole 8a of the first cap 8 constitute a reception portion 10 for liquid-tightly receiving an insertion portion 16 of an endoscope 15 shown in FIG. 2 therein.

Figure 1:
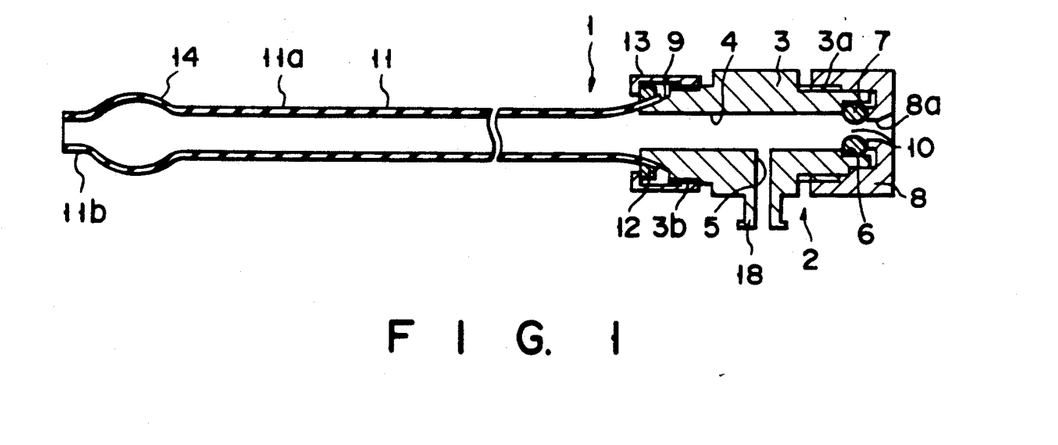
FIG. 1 is a sectional view of a catheter.

A tapered portion 9 and a second threaded portion 3b are sequentially formed on the outer surface at the distal end portion of the body 3. The proximal end of a cylindrical tube-like catheter 11 is fitted on the outer surface of the tapered portion 9. The catheter 11 is made of an elastic material such as silicone rubber or polyurethane rubber. A press ring 12 is fitted on the tapered portion 9 such that the proximal end of the catheter 11 is clamped between the ring 12 and the tapered portion 9. A second cap 13 is threadably engaged with the second threaded portion 3b to urge the press ring 12. As the second cap 13 is screwed in, the press ring 12 moves along the tapered portion 9. As a result, the proximal end of the catheter 11 is urged/held between the ring 12 and the tapered portion 9.

A balloon 14 which can be inflated outward, i.e., radially is arranged near the distal end of the catheter 11. In order to allow the balloon 14 to be easily inflated, the balloon 14 is constituted by a portion of the catheter 11 which is thinner than the remaining portion thereof or a material, such as silicone rubber or polyurethane rubber, which is more elastic than the remaining portion. In addition, both the ends of the balloon 14 are fused to the remaining portion of the catheter 11.

Figure 2:
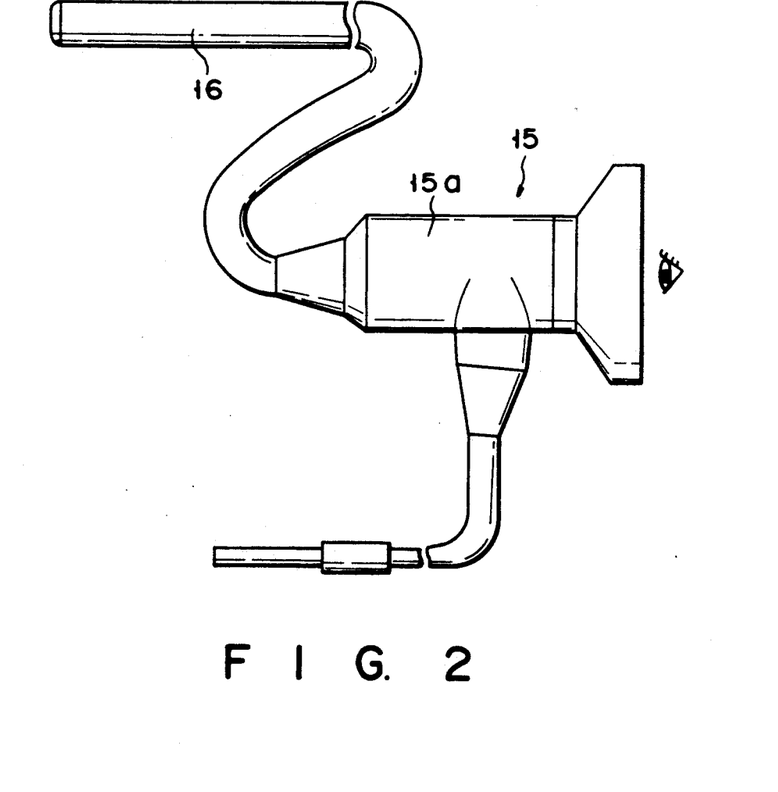
FIG. 2 is a side view of an endoscope.

The inner diameters of a first cylindrical portion located nearer to the proximal end of the catheter than the balloon 14, i.e., a proximal end portion 11a and of the first path 4 are set to be larger than the outer diameter of the cylindrical insertion portion 16 of the endoscope 15 shown in FIG. 2. The inner diameter of a second cylindrical portion located nearer to the distal end of the catheter 11 than the balloon 14 is set to be substantially equal to or slightly smaller than the outer diameter of the insertion portion 16. With this arrangement, when the insertion portion 16 whose proximal end is connected to an operating portion 15a of the endoscope 15 is inserted in the catheter 11 through the reception portion 10 of the manipulating section 2 as shown in FIGS. 3 to 6, a gap 17 is defined between the insertion portion 16 and the proximal end portion 11a, which is located nearer to the proximal end of the catheter 11 than the balloon 14. In contrast to this, a distal end portion 11b, which is located nearer to the distal end of the catheter 11 than the balloon 1 is brought into tight contact with the outer surface of the insertion portion 16. A liquid-tight seal is provided between the distal end portion 11b and the outer surface of the insertion portion 16.

Figure 3:
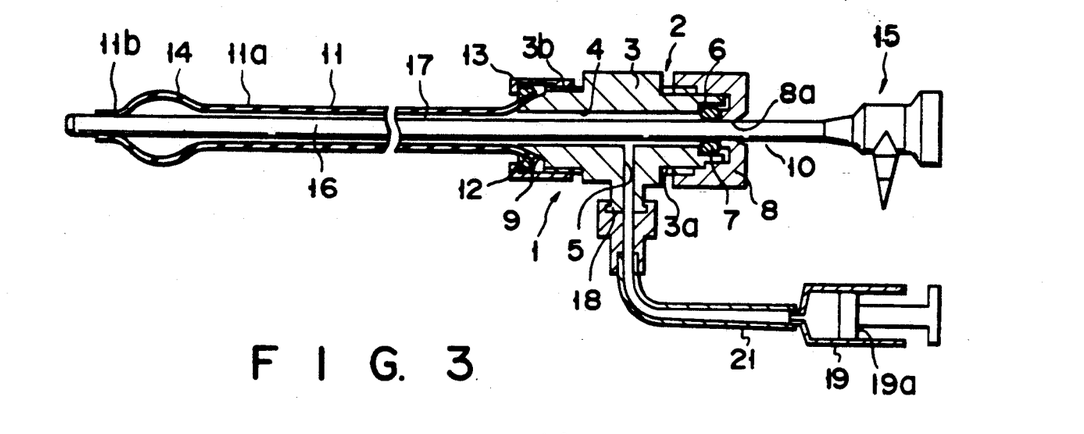
FIG. 3 is a sectional view showing a state wherein the catheter is inserted in the endoscope.

One end of the second path 5 formed in the body 3 of the manipulating section 2 communicates with the liquid path 17 which is an annular gap between the catheter 11 and the insertion portion 16 through the first path 4. The other end of the second path 5 is open to a mouthpiece 18 protruding from the outer surface of the body 3. As shown in FIG. 3, one end of a tube 21 having the other end connected to a transparent liquid inject/supply means, e.g., a cylinder 19 is connected to the mouthpiece 18. A piston 19a is inserted in the cylinder 19, so that a physiological saline solution in the cylinder 19 can be fed into the gap 17 by depressing the piston 19a.

A case wherein the balloon catheter apparatus 1 having the above-described arrangement is used will be described below. The insertion portion 16 of the endoscope 15 is inserted into the catheter 11 through the reception portion 10 of the manipulating section 2 until the distal end portion of the insertion portion 16 protrudes from the distal end of the catheter 11, as shown in FIG. 3. In this state, the catheter 11 is inserted in, e.g., a blood vessel 25 as a vessel cavity shown in FIGS. 4 to 6 toward its upstream side.

Figure 4:
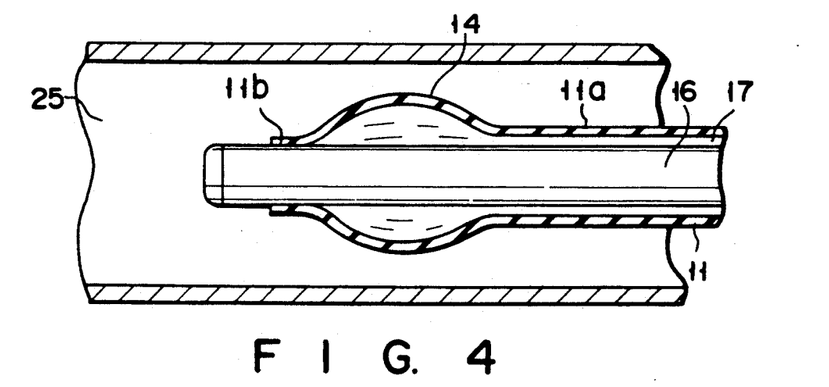
FIGS. 4 to 6 are views respectively showing states of an apparatus of the present invention in use.

When the distal end of the insertion portion 16 is inserted to a predetermined position and observation is performed at this position, the piston 19a of the cylinder 19 filled with a physiological saline solution as a transparent liquid is depressed. The physiological saline solution in the cylinder 19 then flows into the balloon 14 through the second and first paths 5 and 4 and the gap 17 between the catheter 11 and the insertion portion 16. As a result, the balloon 14 is filled with the physiological saline solution, as shown in FIG. 4.

Figure 5:
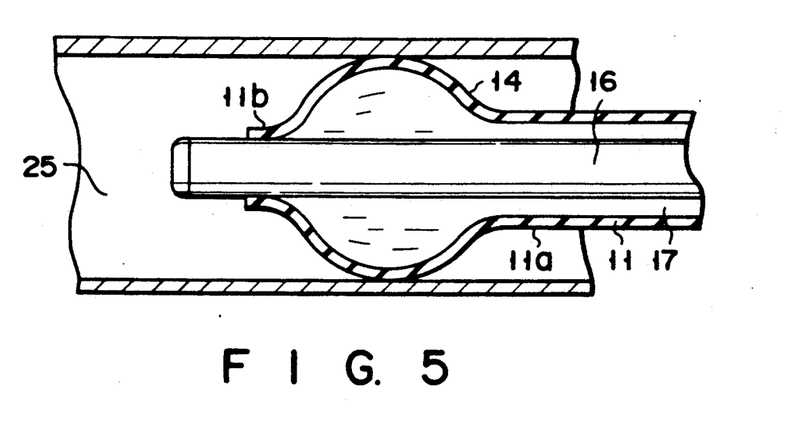
Figure 6:
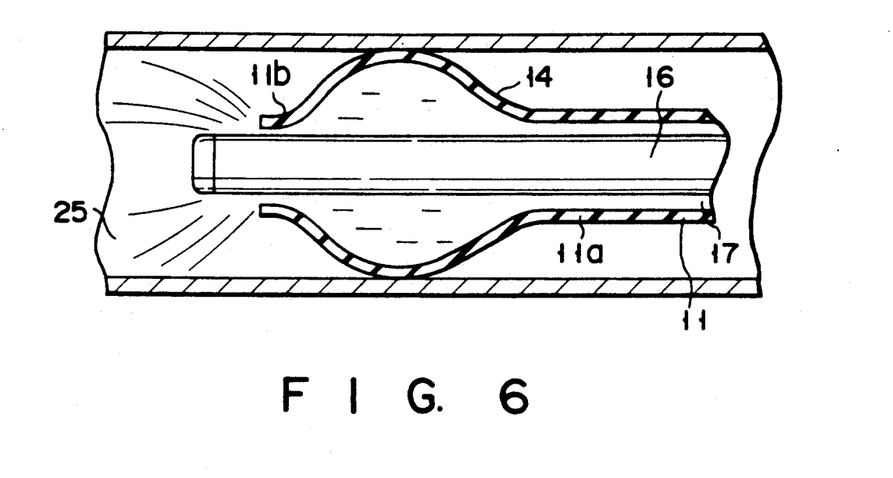

If the piston 19a of the cylinder 19 is further depressed in this state so as to feed the physiological saline solution to the gap 17, the pressure in the catheter 11 is increased, and the outer surface of the balloon 14 of the catheter which is most easily inflated is urged against the inner surface of the blood vessel 25, as shown in FIG. 5. As a result, blood flowing from the right to the left in FIG. 5 is blocked. If the piston 19a of the cylinder 19 is further depressed to inject the physiological saline solution into the gap 17 while the blood flow is blocked in such a manner, the distal end portion 11b, which is located nearer to the distal end of the catheter than the balloon 14, is inflated radially outward, as shown in FIG. 6. As a result, the physiological saline solution starts leaking from the distal end of the catheter 11 and flows to the distal end side of the insertion portion 16, and the blood is replaced with the physiological saline solution at the distal end side of the insertion portion 16. Consequently, the field of view of the endoscope 15 becomes transparent, and observation can be satisfactorily performed. The inner diameter, elasticity, and the like of the distal end portion 11b are set so as not to deflate the balloon 14 to such a degree as to fail to block a blood flow when the physiological saline solution flows out from the catheter 11.

When the field of view of the endoscope 15 is ensured in this manner, depression of the piston 19a of the cylinder 19 is stopped. While the pressure in the balloon 14 is kept high, the physiological saline solution keeps flowing out. When the pressure is decreased, a seal state in which the distal end portion 11b of the catheter 11 is in tight contact with the outer surface at the distal end portion of the insertion portion 16, as shown in FIG. 5, is obtained to stop the blood flow.

If the piston 19a of the cylinder 19 is pulled out, part of the physiological saline solution in the balloon 14 returns to the cylinder 19. As a result, the balloon 14 is deflated to a degree shown in FIG. 4.

That is, according to the above-described balloon catheter apparatus 1, by only feeding a physiological saline solution into the balloon 14, a blood flow can be stopped and the blood in the observation field can be replaced with the physiological saline solution so as to ensure a field of view.

Figure 7:
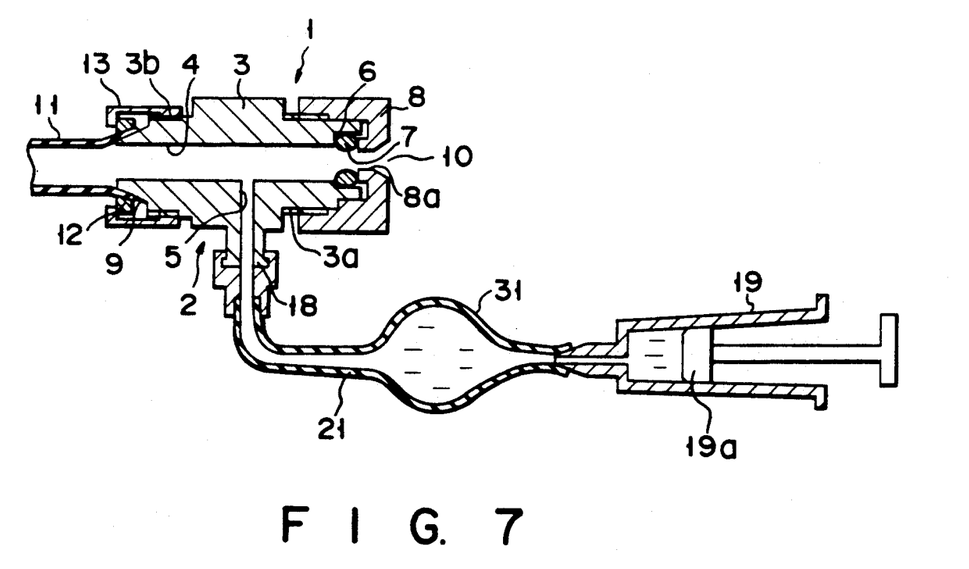
FIG. 7 is a sectional view showing a connection between a catheter according to the second embodiment of the present invention and a syringe.

FIG. 7 shows the second embodiment of the present invention. In this embodiment, an inflatable portion 31 for setting a pressure is formed midway along a tube 21 for causing a cylinder 19 to communicate with a path 5 of a manipulating section 2. The inflatable portion 31 is designed to be inflated when the pressure of a physiological saline solution to be fed to a catheter 11 exceeds a predetermined value. With this arrangement even if depression of a piston 19a of the cylinder 19 cannot be performed in a constant state, a constant pressure can be applied to the physiological saline solution in the catheter 11 because of the compression pressure of the inflatable portion 31. Therefore, the physiological saline solution can be fed to the catheter 11 with slight pressure variations. That is, inflation of a balloon 14 and injection of a physiological saline solution from the distal end of the catheter 11 can be smoothly performed.

Figure 8:
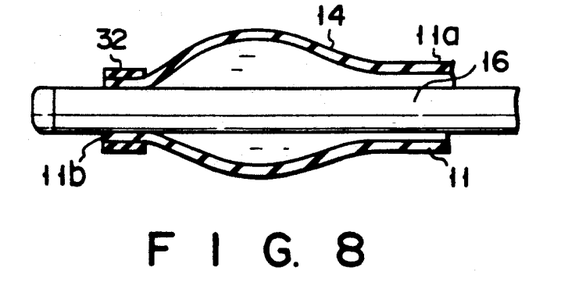
FIGS. 8 to 10 are sectional views respectively showing the distal end portions of catheters according to the third to fifth embodiments of the present invention.

FIG. 8 shows the third embodiment of the present invention. In this embodiment, a ring 32 consisting of an elastic material such as rubber is fitted on the outer surface of a distal end portion 11b which is located nearer to the distal end of a catheter 11 than a balloon 14. With this arrangement, even if the diameter of an insertion portion 16 changes, the distal end portion 11b of the catheter 11 can be brought into tight contact with the insertion portion 16 because of the compression force of the ring 32. In addition, by changing the compression force of the ring 32, the injection amount of a physiological saline solution can be adjusted. If the diameter of a vessel cavity changes, the inflation degree of the balloon 14 can be adjusted. For example, if the diameter of the vessel cavity is increased, the balloon 14 can be inflated more to be brought into tight contact with the vessel cavity by increasing the elastic force of the ring 32.

Figure 9:
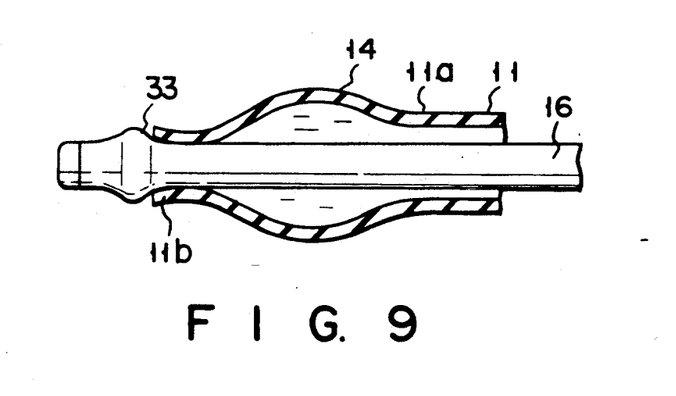

FIG. 9 shows the fourth embodiment of the present invention. In this embodiment, an annular projection 33 is formed at the distal end portion of an insertion portion 16 so as to have a larger diameter than the remaining portion. The amount of a physiological saline solution flowing out from the distal end of a catheter 11 can be adjusted by axially moving the insertion portion 16 and the catheter 11 in the opposite directions. More specifically, if the catheter 11 or the insertion portion 16 is slid to cause the distal end of the catheter 11 to be fitted on the projection 33, injection of a physiological saline solution from the contact portion between these portions become difficult. If the distal end of the catheter 11 is located before the projection 33, injection of a physiological saline solution from the distal end of the catheter 11 becomes easy compared with the case wherein the distal end is fitted on the projection 33. Therefore, the injection amount of a physiological saline solution can be adjusted by relative movement between the catheter 11 and the insertion portion 16. In addition, if the distal end of the catheter 11 is fitted on the projection 33 while the distal end of the catheter 11 is located before the projection 33 and a physiological saline solution is injected, the injection of the physiological saline solution can be stopped. In contrast to this, if the distal end of the catheter 11 is slid to be separated from the projection 33, the physiological saline solution can be injected.

Figure 10:
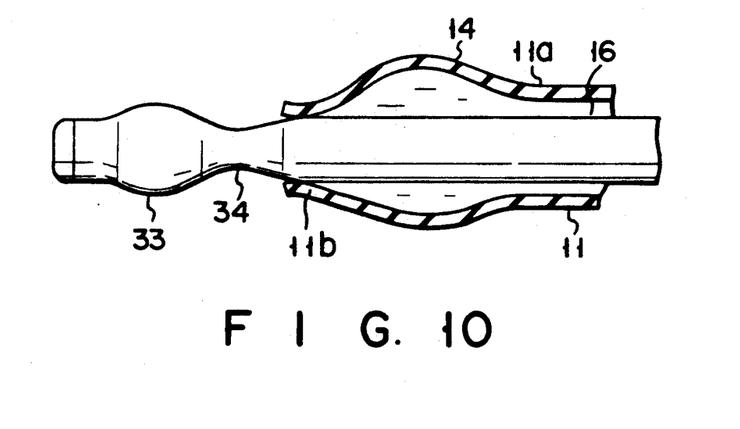

FIG. 10 shows the fifth embodiment of the present invention. This embodiment is similar to the fourth embodiment in formation of an annular projection 33 at the distal end portion of an insertion portion 16, but is different therefrom in formation of an annular projection 34 before the projection 33. According to such an arrangement, even if the pressure of a physiological saline solution in a balloon 14 is not very high, the solution can be injected from the distal end of the catheter 11 by setting a distal end portion 11b of the catheter 11 at the position of the projection 34. Therefore, the inflation degree of the balloon 14 can be easily adjusted.

In any of the above-described embodiments, the balloon catheter apparatus of the present invention is used in combination with an endoscope for observing a vessel cavity. However, the present invention is not limited to such a combination. The balloon catheter apparatus of the present invention can be used in combination with other body cavity insertion devices to be inserted in body cavities and perform predetermined functions. Such cases will be described below.

Figure 11:
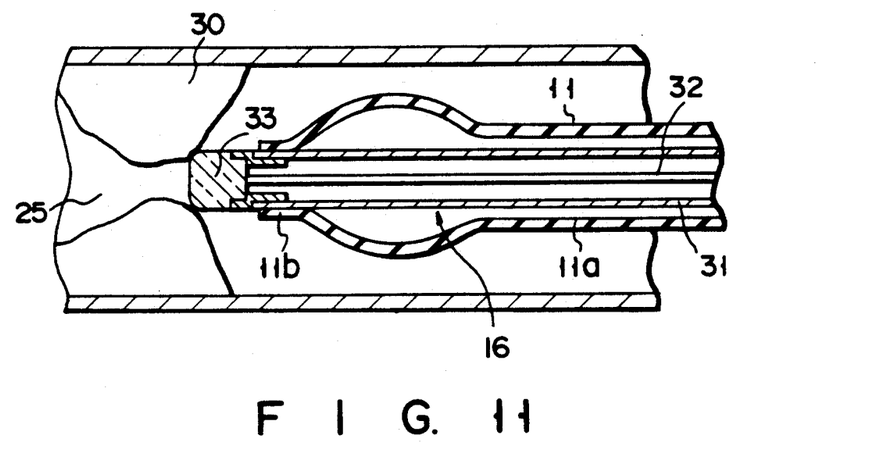
FIGS. 11 and 12 are sectional views respectively showing catheters according to the sixth and seventh embodiments of the present invention together with body cavity treating devices.

FIG. 11 shows a case wherein a laser probe is used as a body cavity insertion device.

A blood vessel blocking substance 30 is sometimes deposited on the inner surface of a blood vessel 25 and blocks a blood flow. In this case, the substance 30 must be removed to restore the blood flow. As a method of performing such a treatment, a method of using a laser probe is known. In this method, a laser beam is radiated onto the substance 30 to evaporate it. This laser probe includes an insertion portion 16 constituted by a cylindrical laser probe sheath 31, a laser guide fiber 32 extending coaxially with the sheath 31 and protected thereby, and a laser chip 33, attached to the distal end of the sheath 31 and optically connected to the fiber 32, for outputting a laser beam from the fiber 32 to the outside. In such a laser probe, a laser beam is guided by the fiber 32 from a laser beam generating device (not shown) located outside the body into a blood vessel 25, and is radiated onto the substance 30 through the laser chip 33, thereby evaporating it. In the laser probe having such an arrangement, the outer diameter of the laser probe sheath 31 is set to be smaller than the inner diameter of a proximal end portion 11a of a catheter 11 and to be equal to or slightly larger than the inner diameter of a distal end portion 11b.

In combination of the above-described laser probe and the catheter apparatus, it is apparent that the insertion portion 16 is inserted into the catheter 11 so as to cause the distal end portion of the insertion portion 16 to protrude in the same manner as in the first embodiment, and blood in a predetermined portion in the blood vessel 25 can be replaced with a transparent liquid by the same operation as in the first embodiment. A laser beam can be radiated onto the substance 30 through the portion in which the blood is replaced with the transparent liquid.

Figure 12:
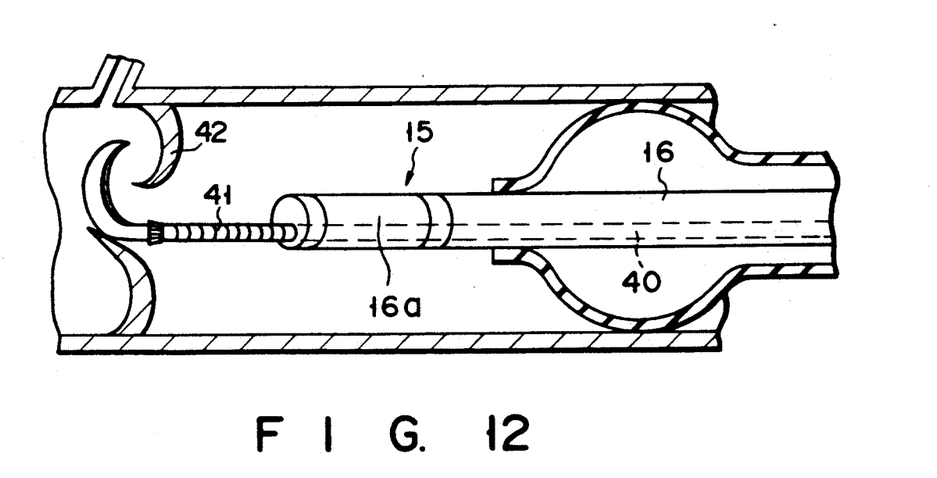

In the seventh embodiment shown in FIG. 12, an endoscope which performs a predetermined treatment in a body cavity as well as observation is used. The distal end portion of an insertion portion 16 of an endoscope 15 has an arcuated portion 16a which can be deflected in a predetermined direction. This arcuated portion 16a can be arcuated at a predetermined degree in a predetermined direction with an operation wire upon a lever operation in an operating section placed outside the body. A channel 40 for inserting a treatment device is formed in the insertion portion 16. The distal end of the channel is open to the distal end face of the arcuated portion 16a, wherein the proximal end of the channel extends to the operating section. A treatment device such as a venous valve cut blade 41 or a laser probe is inserted in the endoscope from the outside of the body through the channel 40 so as to cause the distal end of the device to protrude from the arcuated portion 16a, thereby allowing a predetermined treatment. If the venous valve cut blade 41 is used, a venous valve 42 of a vein can be cut while directly observing a corresponding portion. It is apparent that in such an endoscope, an operation of replacing blood with a transparent liquid can be performed in the same manner as in the first embodiment.

According to the above-described apparatus of the present invention, a blood flow in a vessel cavity can be blocked and a field of view can be ensured by simply injecting a transparent liquid or the like into the catheter through the feed port. Therefore, operability can be improved as compared with the conventional apparatus in which blocking of a blood flow and ensuring of a field of view are achieved by different operations. In addition, in the structure of the present invention, the insertion portion of an insertion device need only be inserted in a catheter, and liquids for inflating a balloon and for ensuring a field of view may be respectively fed through different tubes as in the conventional apparatus.

What is claimed is:

1. A combination of a body cavity insertion device and a balloon catheter apparatus, said body cavity insertion device comprising an insertion portion to be inserted in a body cavity through said balloon catheter apparatus, said insertion portion having a distal end portion; and said balloon catheter apparatus comprising a catheter to be inserted in the body cavity, said catheter including an elongated tube defining a reception portion, in which said insertion portion is insertable, said tube including a balloon portion which is inflatable under pressure of liquid in said reception portion so as to seal the body cavity, a liquid flow path communicating said reception portion with said balloon portion, and a seal portion, which is connected to said balloon portion, and through which a distal end portion of said insertion portion is caused to protrude outward, said seal portion including means for normally sealing said liquid within the catheter and being opened by said liquid in said balloon portion after the body cavity is sealed by said balloon portion as pressure of said liquid exceeds a predetermined value so as to feed the pressurized liquid in said balloon portion, toward the distal end portion of said insertion portion.

2. A combination according to claim 1, wherein said sealing means comprises a cylindrical elastic member which is brought into elastic contact with an outer surface of said insertion portion so as to provide a seal between said catheter and said insertion portion.

3. A combination according to claim 2, wherein said insertion portion of said body cavity insertion device comprises an annular projection at a distal end portion which can be brought into contact with said seal portion of said catheter.

4. An apparatus according to claim 1 wherein said reception portion has an inner diameter larger than an outer diameter of said insertion portion, at least a portion of said liquid flow path is formed between said reception portion and said insertion portion, and said means for normally sealing said liquid within the catheter having an elastic seal portion which is adapted to be brought into elastic contact with said reception portion.

5. An apparatus according to claim 1, further comprising feed means for feeding the liquid to said liquid flow path, said feed means including a cylinder in which the liquid is stored, a tube for coupling said cylinder to said liquid flow path, and a piston for increasing a pressure of the liquid in said cylinder in cooperation with said cylinder and feeding the liquid to said liquid flow path through said tube.

6. An apparatus according to claim 5, wherein said tube comprises an elastic balloon which is inflated in accordance with a liquid pressure in said tube when the liquid pressure exceeds a predetermined liquid pressure.

7. A balloon catheter apparatus for use with a device having a cylindrically shaped insertion portion adapted to be inserted in a body cavity, comprising:

a manipulating section having a reception portion adapted for receiving said insertion portion therein, and a liquid port in fluid communication with said reception portion; and a catheter including a first portion, a balloon portion, and a second portion, said first and second portions being cylindrically shaped, with said first portion being connected between said manipulating section and said balloon portion, and said balloon portion being connected between said first and second portions, said catheter being adapted to receive the insertion portion therein as it extends from the reception portion to have its tip protruding outside of said first portion, said first portion being sized relative to said insertion portion to form with said insertion portion a liquid flow path to said balloon portion, said balloon portion being inflatable under pressure of liquid in said liquid flow path, and wherein said second portion includes means for forming a liquid tight seal with said insertion portion while pressure in said liquid flow path is below a predetermined value, and for releasing said seal by liquid from said liquid flow path so that liquid flows out of the second portion of said catheter when pressure in said liquid flow path is at least at said predetermined value.

8. An apparatus according to claim 7 wherein said first portion has an inner diameter larger than an outer diameter of said insertion portion, at least a portion of said liquid path is formed between said first portion and said insertion portion, and the seal forming means of said second portion having an elastic seal portion which is adapted to be brought into elastic contact with said insertion portion.

9. An apparatus according to claim 8, wherein said elastic seal portion comprises an elastic ring, detachably mounted on said second portion, for changing an elastic force of said seal portion.

10. An apparatus according to claim 7, further comprising feed means for feeding the liquid to said liquid port, said feed means including a cylinder in which the liquid is stored, a tube for connecting said cylinder to said liquid port, and a piston for increasing a pressure of the liquid in said cylinder in cooperation with said cylinder and feeding the liquid to said liquid port through said tube.

11. An apparatus according to claim 10, wherein said tube comprises an elastic balloon which is inflated in accordance with a liquid pressure in said tube when the liquid pressure exceeds a predetermined liquid pressure.

12. A method of operating a balloon catheter apparatus, comprising the steps of:

mounting a body cavity insertion device to a balloon catheter by (a) inserting an insertion section of the insertion device into a first insertion portion of the catheter, and (b) stopping the inserting step (a) when a distal end portion of the insertion device projects from a distal end of the catheter;

inserting the balloon catheter into a body cavity;

performing observation by the sequential steps of (a) connecting a syringe to a liquid port of the catheter, (b) injecting liquid through the syringe to a liquid flow path in communication with a balloon of the catheter so as to inflate said balloon while maintaining a seal which prevents flow of said liquid from the catheter into said body cavity, (c) causing the inflated balloon to interrupt a blood flow, (d) further injecting liquid so as to increase the internal pressure of the balloon to release said seal and, thus, to discharge the liquid from the catheter into said body cavity, and (e) performing a desired observation; and withdrawing the balloon catheter from the body cavity.

* * * * *